(12) United States Patent
Raney et al.

(10) Patent No.: US 7,462,730 B2
(45) Date of Patent: *Dec. 9, 2008

(54) BRANCHED ESTER COMPOSITION

(75) Inventors: Kirk Herbert Raney, Houston, TX (US); Arie Van Zon, Amsterdam (NL); Marijke De Boer-Wildschut, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/929,080

(22) Filed: Aug. 27, 2004

(65) Prior Publication Data

US 2005/0048091 A1 Mar. 3, 2005

Related U.S. Application Data

(60) Provisional application No. 60/498,520, filed on Aug. 28, 2003.

(51) Int. Cl.
*C07C 53/00* (2006.01)

(52) U.S. Cl. ............... 554/227; 424/401; 514/552; 514/556; 514/844; 514/847; 514/873

(58) Field of Classification Search ............... 514/552, 514/556, 844, 847, 873; 424/401; 554/227
See application file for complete search history.

(56) References Cited

U.S. PATENT DOCUMENTS

| | | | |
|---|---|---|---|
| 4,634,719 A | 1/1987 | Takaishi et al. | 514/772 |
| 5,656,664 A * | 8/1997 | O'Lenick, Jr. | 514/552 |
| 5,686,087 A | 11/1997 | Ansmann et al. | 424/401 |
| 5,780,694 A | 7/1998 | Singleton | 568/909 |
| 5,849,960 A * | 12/1998 | Singleton et al. | 568/909 |
| 5,997,854 A | 12/1999 | von Mallek | 424/70.19 |
| 6,150,322 A * | 11/2000 | Singleton et al. | 510/426 |
| 6,335,312 B1 | 1/2002 | Coffindaffer et al. | 510/159 |
| 6,531,143 B1 * | 3/2003 | Yakumaru et al. | 554/121 |
| 2004/0042988 A1 | 3/2004 | Raney et al. | 424/70.1 |
| 2004/0076654 A1 * | 4/2004 | Vinson et al. | 424/401 |
| 2005/0196362 A1 | 9/2005 | Carty et al. | 424/59 |

FOREIGN PATENT DOCUMENTS

| | | |
|---|---|---|
| DE | 195 45 789 A1 | 6/1997 |
| WO | WO 97/39089 | 10/1997 |
| WO | WO9823566 | 6/1998 |
| WO | WO 99/18928 | 4/1999 |
| WO | WO 99/18929 | 4/1999 |
| WO | 00/03680 | 1/2000 |
| WO | WO 01/89466 A1 | 11/2001 |
| WO | 2004/022013 A1 | 3/2004 |
| WO | 2004/022029 A2 | 3/2004 |

OTHER PUBLICATIONS

International Search Report for PCT/US2004/027737 of Mar. 18, 2005.
Written Opinion for PCT/US204/027737 of Mar. 18, 2005.
"Guerbet Alcohols A Versatile Hydrophobe," Soap/Cosmetics/Chemical Specialties for Apr. 1987, Mac.Nair-Dorland Co. New York, US, pp. 52, 54-55, 115, XP-00097151.
PCT Written Opinion for PCT—International Patent Application No. PCT/US 03/27127.
International Search Report for PCT of Jan. 20, 2004.
International Search Report for PCT/US2005/006551 of Jun. 15, 2005.
Written Opinion for PCT/US2005/006551 of Jun. 15, 2005.

* cited by examiner

*Primary Examiner*—Deborah D Carr
(74) *Attorney, Agent, or Firm*—Donald F. Haas

(57) ABSTRACT

A branched ester composition obtainable by the reaction of a carboxylic acid with a branched alcohol composition under esterification reaction conditions wherein the branched alcohol composition has from about 8 to about 36 carbon atoms and an average number of branches per molecule of from about 0.7 to about 3.0, said branching comprising methyl and ethyl branches. The present invention further relates to personal care compositions for topical application to the skin or hair comprising said branched ester composition. The branched ester composition of the invention provides improved formulation flexibility.

15 Claims, No Drawings

BRANCHED ESTER COMPOSITION

This application claims the benefit of U.S. Provisional Application No. 60/498,520 filed Aug. 28, 2003, the entire disclosure of which is hereby incorporated by reference.

FIELD OF THE INVENTION

The present invention relates to a new ester composition which is derived from the reaction of a carboxylic acid with a highly branched primary alcohol composition. The present invention also relates to personal care compositions for topical application to the skin or hair comprising this ester composition.

BACKGROUND OF THE INVENTION

Personal care compositions such as skin moisturizing creams, sunscreens, antiperspirants, shampoos, and the like, commonly contain long chain fatty acids and esters. A commonly used linear fatty acid ester in this regard is cetearyl stearate. A commonly used branched fatty acid ester is isocetyl stearate. Such ester materials are useful for providing skin conditioning benefits such as moisturization, humectancy, emolliency, visual improvement of the skin surface, soothing and softening of the skin, improvement in skin feel and the like. Other benefits afforded by long chain fatty acid esters include viscosity and rheology modification.

Cetearyl stearate and isocetyl stearate have different physical characteristics largely due to their differing structural characteristics, namely that cetearyl stearate is a linear fatty acid ester whereas isocetyl stearate is a branched fatty acid ester. For example, cetearyl stearate is typically supplied and shipped as flakes or some other solid form and has a melting point range of about 54° C. to 65° C. This means that it should be converted to a liquid by heating before it can be formulated into personal care compositions. On the other hand, isocetyl stearate, derived from a so-called "Guerbet" alcohol which contains some alkyl branching, is typically liquid at room temperature and has a melting point of about –10° C. The majority of the branching in the "Guerbet" alcohol from which the ester is derived is at the $C_2$ position on the carbon chain. In addition, the alkyl branches tend to be long chain branches, such as $C_4$ and above.

Further, isocetyl stearate is more soluble at room temperature in nonpolar solvents than cetearyl stearate.

Although isocetyl stearate overcomes the solubility problems associated with linear esters of the cetearyl stearate type, it is unfortunately relatively difficult to manufacture. Firstly, a Guerbet alcohol has to be produced which involves the preparation of an aldehyde followed by an aldol condensation. It would therefore be desirable to provide an ester compound which ameliorates the solubility problems of linear esters such as cetearyl stearate, while at the same time being easier to manufacture than esters derived from branched Guerbet alcohols.

Further, from the viewpoint of improving formulation flexibility, it would be desirable to provide a long chain ester having physical properties in between that of the linear cetearyl stearate type ester and the branched isocetyl stearate type ester. In particular it would be desirable to provide a long chain ester having a physical form which is somewhere in between a solid flake and a homogeneous liquid, and having a melting point intermediate of that of cetearyl stearate and isocetyl stearate. In addition to affecting handling characteristics in commercial settings, the melting point properties of esters used as emollients have been related to the resulting skin feel of the product, with fully liquid emollient ingredients providing a "light" skin feel while solid emollient ingredients result in a "heavy, long-lasting" skin feel.

It has now surprisingly been found that the particular branched ester composition of the present invention which is derived from a branched primary alcohol composition having from 0.7 to 3.0 branches per molecule said branching comprising methyl and ethyl branches has physical properties which are intermediate between cetearyl stearate and isocetyl stearate type esters. This is advantageous for providing an improvement in formulation flexibility. In addition, it has surprisingly been found that the branched ester composition of the present invention helps to overcome the problems of high melting points and low solubility associated with the linear cetearyl stearate type esters while at the same time being easier to manufacture than the branched isocetyl stearate type esters derived from Guerbet alcohols.

U.S. Pat. No. 5,849,960 (Shell Oil Company) discloses a branched primary alcohol composition having from 8 to 36 carbon atoms which contains an average number of branches per molecule of at least 0.7, said branching comprising methyl and ethyl branching. These alcohols can subsequently be converted to anionic or nonionic detergents or general surfactants by sulfonation or ethoxylation, respectively, of the alcohol. The detergents produced exhibit useful properties such as high biodegradability and high cold water detergency. No disclosure is provided in U.S. Pat. No. 5,849,960 of esters derived from these alcohols, nor the use of these branched alcohols or esters derived therefrom in personal care compositions.

Co-pending U.S. patent application Ser. No. 60/407,724 discloses the use of such alcohols as emollients in personal care compositions.

WO99/18929, WO99/18928 and WO97/39089 (The Procter and Gamble Company) disclose personal cleansing compositions comprising mid-chain branched surfactants. The mid-chain branched surfactants are manufactured from mid-chain branched alcohols. The formulations therein however do not contain any mention of esters derived from these mid-chain branched alcohols per se, only the corresponding surfactants. In addition, these documents are concerned with cleansing compositions having relatively high levels of surfactant ingredients.

SUMMARY OF THE INVENTION

According to the present invention there is provided a branched ester composition obtainable by the reaction of a carboxylic acid with a branched alcohol composition under esterification reaction conditions wherein the branched primary alcohol composition has from about 8 to about 36 carbon atoms and an average number of branches per molecule of from about 0.7 to about 3.0, said branching comprising methyl and ethyl branches.

According to a further aspect of the present invention there is provided the use of a branched ester composition obtainable by the reaction of a carboxylic acid with a branched alcohol composition wherein the branched alcohol composition has from about 8 to about 36 carbon atoms and an average number of branches per molecule of from about 0.7 to about 3.0, said branching comprising methyl and ethyl branches, for providing emolliency benefits to the skin.

According to yet a further aspect of the present invention there is provided a personal care composition comprising:
(i) a branched ester composition obtainable by the reaction of an organic acid with a branched alcohol composition under esterification reaction conditions wherein the branched alcohol composition has from about 8 to about 36 carbon atoms and an average number of branches per molecule of from about 0.7 to about 3.0, said branching comprising methyl and ethyl branches; and (ii) a cosmetically acceptable vehicle.

According to yet a further aspect of the present invention there is provided a branched ester composition comprising at least one ester compound of formula RCOOR' wherein R is a straight chain or branched, substituted or unsubstituted, alkyl or alkenyl group having from about 1 to about 30 carbon atoms or a substituted or unsubstituted cycloaromatic group having from about 6 to about 14 carbon atoms and wherein R' is an alkyl or alkenyl group having from about 8 to about 36 carbon atoms and wherein said R' group has an average number of branches per molecule of from about 0.7 to about 3.0, said branching on the R' group comprising methyl and ethyl branches.

The ester compositions of the present invention provide improvements in formulation flexibility, especially in the formulation of personal care compositions. In addition, the ester compositions of the present invention help to overcome the solubility and physical property problems of linear esters of the cetearyl stearate type while being easier to manufacture than esters derived from branched "Guerbet" alcohols.

Further the esters of the present invention exhibit good emolliency, skin feel, skin softening, application and moisturizing properties together with good viscosity and rheology characteristics. The particular branched esters used in the present compositions are also highly biodegradable.

DETAILED DESCRIPTION OF THE INVENTION

All percentages and ratios used herein are by weight of the total personal care composition, unless otherwise specified.

All publications cited herein are incorporated by reference in their entirety, unless otherwise indicated.

The term "cosmetically-acceptable", as used herein, means that the compositions, or components thereof, are suitable for use in contact with human skin or hair without undue toxicity, incomparability, instability, allergic response, and the like.

The term "safe and effective amount" as used herein means an amount of a compound, component, or composition sufficient to significantly induce a positive benefit, preferably a positive skin appearance or feel benefit, including independently the benefits disclosed herein, but low enough to avoid serious side effects, i.e. to provide a reasonable benefit to risk ratio, within the scope of sound medical judgment.

The branched ester composition of the present invention is described below in more detail.

Branched Ester Composition

The branched ester composition of the present invention is obtainable by the reaction of a carboxylic acid and a branched primary alcohol composition under esterification reaction conditions.

Any carboxylic acid suitable for use in preparing ester compounds is suitable herein.

Suitable carboxylic acids for use herein include, but are not necessarily limited to, straight chain or branched, substituted or unsubstituted, saturated or unsaturated, aliphatic carboxylic acids having from 1 to 30 carbon atoms (the number of carbon atoms not including the carboxyl group), preferably from 10 to 22 carbon atoms, more preferably from 12 to 18 carbon atoms, and substituted or unsubstituted cycloaromatic carboxylic acids having from 6 to 14, preferably 6 carbon atoms in the aromatic ring.

Suitable substituents on the aliphatic carbon chain of aliphatic carboxylic acids include —OH, F, Cl, Br, I, —NH$_2$ and phenyl. Aliphatic carboxylic acids substituted with a hydroxy group at the alpha or beta position on the aliphatic carbon chain are known as alpha-hydroxy acids and beta-hydroxy acids, respectively.

Suitable substituents on the aromatic ring of the cycloaromatic carboxylic acids include $C_1$-$C_4$ alkyl groups, —OH, F, Cl, Br, I, and —NH$_2$, preferably $C_1$-$C_4$ alkyl, especially methyl and ethyl.

Examples of suitable carboxylic acids for use herein include those listed in the CTFA (Cosmetics, Toiletries and Fragrances Association) Buyers Guide 2001. Particular examples of suitable carboxylic acids for use herein include lauric acid, myristic acid, palmitic acid, oleic acid, linoleic acid, stearic acid, behenic acid, benzoic acid, alkylated benzoic acids, isostearic acid, isodecanoic acid, isoethylhexanoic acid, salicylic acid, ricinoleic acid, and mixtures thereof.

A preferred class of carboxylic acids for use herein are straight chain, saturated, aliphatic carboxylic acids having from 10 to 22 carbon atoms (the number of carbon atoms excluding the carboxyl group). An especially preferred carboxylic acid of this type is stearic acid.

Another preferred class of carboxylic acids for use herein is substituted or unsubstituted aromatic carboxylic acids, particularly those having 6 carbon atoms in the aromatic ring. An especially preferred carboxylic acid of this type is benzoic acid.

Care should be taken to handle the alcohols in such a way that the desired ester product is obtained. For example, in the case of hydroxy carboxylic acids, the person skilled in the art will appreciate that measures have to be taken to protect the hydroxy substituent before reacting the hydroxy carboxylic acid with an alcohol in an esterification reaction. Similarly, in the case of unsaturated aliphatic carboxylic acids (e.g. linoleic acid), the person skilled in the art will appreciate that carbon-carbon double bonds are susceptible to oxidation and therefore suitable precautions should be taken in the personal care formulation to prevent oxidation of these double bonds (e.g. by addition of an antioxidant to the personal care formulation).

The branched primary alcohol composition for use in the preparation of the ester herein is a branched primary alcohol composition having from 8 to 36 carbon atoms and an average number of branches per molecule of from 0.7 to 3.0, said branching comprising methyl and ethyl branching.

As used herein, the phrase "average number of branches per molecule chain" refers to the average number of branches per alcohol molecule, as measured by $^{13}$C Nuclear Magnetic Resonance ($^{13}$C NMR) as discussed below, or optionally $^1$H Proton NMR. The average number of carbon atoms in the chain is determined by gas chromatography with a mass selective detector.

Various references will be made throughout this specification and the claims to the percentage of branching at a given carbon position, the percentage of branching based on types of branches, average number of branches, and percentage of quaternary atoms. These amounts are to be measured and determined by using a combination of the following three $^{13}$C-NMR techniques. (1) The first is the standard inverse gated technique using a 45-degree tip $^{13}$C pulse and 10 s recycle delay (an organic free radical relaxation agent is added to the solution of the branched alcohol in deuterated chloroform to ensure quantitative results). (2) The second is a J-Modulated Spin Echo NMR technique (JMSE) using a 1/J delay of 8 ms (J is the 125 Hz coupling constant between carbon and proton for these aliphatic alcohols). This sequence distinguishes carbons with an odd number of protons from those bearing an even number of protons, i.e. $CH_3/CH$ vs $CH_2/Cq$ (Cq refers to a quaternary carbon). (3) The third is the JMSE NMR "quat-only" technique using a 1/2J delay of 4 ms which yields a spectrum that contains signals from quaternary carbons only. The JSME NMR quat only technique for detecting quaternary carbon atoms is sensitive enough to detect the presence of as little as 0.3 atom % of quaternary carbon atoms. As an optional further step, if one desires to confirm a conclusion reached from the results of a quat only JSME NMR spectrum, one may also run a DEPT-135 NMR sequence. We have found that the DEPT-135 NMR sequence is very helpful in differentiating true quaternary carbons from break-through protonated carbons. This is due to the fact that the DEPT-135 sequence produces the "opposite" spectrum to that of the JMSE "quat-only" experiment. Whereas the latter nulls all signals except for quaternary carbons, the DEPT-135 nulls exclusively quaternary carbons. The combination of the two spectra is therefore very useful in spotting non quaternary carbons in the JMSE "quat-only" spectrum. When referring to the presence or absence of quaternary carbon atoms throughout this specification, however, we mean that the given amount or absence of the quaternary carbon is as measured by the quat only JSME NMR method. If one optionally desires to confirm the results, then also using the DEPT-135 technique to confirm the presence and amount of a quaternary carbon.

The primary alcohol used in the preparation of the ester compound of the invention contains an average chain length per molecule ranging from about 8 to about 36 carbon atoms, preferably from about 11 to about 21 carbon atoms. The number of carbon atoms includes carbon atoms along the chain backbone as well as branching carbons, but does not include carbon atoms in alkylene oxide groups.

Preferably, at least 75 wt %, more preferably, at least 90 wt. % of the molecules in the primary alcohol have chain lengths ranging from 11 to 21, yet more preferably from 14 to 18 carbon atoms.

The average number of branches per alcohol molecule is at least 0.7, as defined and determined above. Preferred alcohols are those having an average number of branches of from 0.7 to 3.0, preferably from 1.0 to 3.0. Particularly preferred alcohols are those having an average number of branches of at least 1.5, in particular ranging from 1.5 to about 2.3, especially from 1.7 to 2.1.

In a preferred embodiment of the invention the primary alcohol has less than 0.5 atom % of Cq's as measured by a quat-only JMSE modified 13C-NMR having a detection limit of 0.3 atom % or better, and preferably contains no Cq's as measured by this NMR technique. Such an alcohol leads to an ester also having this low level of quaternary carbon atoms. For reasons not yet clearly understood, it is believed that the presence of Cq's on an alcohol molecule prevents the biodegradation by biological organisms. Alcohols containing as little as 1 atom % of Cq's have been been found to biodegrade at failure rates.

In a preferred embodiment of the invention, less than 5%, or more preferably less than 3%, of the alcohol molecules in the primary alcohol are linear alcohols. The efficient reduction in the number of linear alcohols to such a small amount results from introducing branching on an olefin feedstock either by a skeletal isomerization or a dimerisation technique using efficient catalysts as described further below, rather than introducing branching by methods such as acid catalyzed oligomerization of propylene molecules, or zeolite catalyzed oligomerization techniques. The percentage of molecules which are linear may be determined by gas chromatography.

Skeletal Isomerization

In a preferred embodiment herein, the branching on the alcohol is introduced by skeletal isomerization.

When the branching has been achieved by skeletal isomerization, the primary alcohol used herein may be characterized by the NMR technique as having from 5 to 25% branching on the C2 carbon position, relative to the hydroxyl carbon atom. In a more preferred embodiment, from 10 to 20% of the number of branches are at the C2 position, as determined by the NMR technique. The primary alcohol also generally has from 10% to 50% of the number of branches on the C3 position, more typically from 15% to 30% on the C3 position, also as determined by the NMR technique. When coupled with the number of branches seen at the C2 position, the primary alcohol contains significant amount of branching at the C2 and C3 carbon positions.

Not only does the primary alcohol used in the present invention have a significant number of branches at the C2 and C3 positions, but we have also seen by the NMR technique that many of the primary alcohols have at least 5% of isopropyl terminal type of branching, meaning methyl branches at the second to last carbon position in the backbone relative to the hydroxyl carbon. We have even seen at least 10% of terminal isopropyl types of branches in the primary alcohol, typically in the range of 10% to 20%. In typical hydroformylated olefins of the NEODOL series commercially available from The Shell Chemical Company, less than 1%, and usually 0.0%, of the branches are terminal isopropyl branches. By skeletally isomerizing the olefin, however, the primary alcohol contains a high percentage of terminal isopropyl branches relative to the total number of branches.

Considering the combined number of branches occurring at the C2, C3, and isopropyl positions, there are embodiments of the invention where at least 20%, more preferably at least 30%, of the branches are concentrated at these positions. The scope of the invention, however, includes branching occurring across the length of the carbon backbone.

The types of branching found in the primary alcohol used herein varies from methyl, ethyl, propyl, and butyl or higher.

In a preferred embodiment of the invention, the total number of methyl branches number at least 40%, even at least 50%, of the total number of branches, as measured by the NMR technique described above. This percentage includes the overall number of methyl branches seen by the NMR technique described above within the C1 to the C3 carbon positions relative to the hydroxyl group, and the terminal isopropyl type of methyl branches.

The primary alcohol component herein contains a significant increase in the number of ethyl branches over those seen on NEODOL alcohols such as NEODOL 45. The number of ethyl branches can range from 5% to 30%, most typically from 10% to 20%, based on the overall types of branching that the NMR method detects. Thus, the skeletal isomerization of the olefins produces both methyl and ethyl branches. Thus, the types of catalysts one may use to perform skeletal isomerization are not restricted to those which will produce only methyl branches. The presence of a variety of branching types is believed to enhance a good overall balance of properties.

The olefins used in the olefin feed for skeletal isomerization are at least $C_7$ mono-olefins. In a preferred range, the olefin feed comprises $C_7$ to $C_{35}$ mono-olefins. Olefins in the $C_{11}$ to $C_{19}$ range are considered most preferred for use herein, to produce primary alcohol components in the $C_{12}$ to $C_{20}$ range.

In general, the olefins in the olefin feed composition are predominantly linear. Attempting to process a predominantly branched olefin feed, containing quaternary carbon atoms or extremely high branch lengths, would require separation methods after passing the olefin stream across the catalyst bed to separate these species from the desired branched olefins. While the olefin feed can contain some branched olefins, the olefin feed processed for skeletal isomerization preferably contains greater than about 50 percent, more preferably greater than about 70 percent, and most preferably greater than about 80 mole percent or more of linear olefin molecules.

The olefin feed generally does not consist of 100% olefins within the specified carbon number range, as such purity is not commercially available. The olefin feed is usually a distribution of mono-olefins having different carbon lengths, with at least 50 wt.% of the olefins being within the stated carbon chain range or digit, however specified. Preferably, the olefin feed will contain greater than 70 wt. %, more preferably about 80 wt.% or more of mono-olefins in a specified carbon number range (e.g., $C_7$ to $C_9$, $C_{10}$ to $C_{12}$, $C_{11}$ to $C_{15}$, $C_{12}$ to $C_{13}$, $C_{15}$ to $C_{18}$, etc.), the remainder of the product being olefin of other carbon number or carbon structure, diolefins, paraffins, aromatics, and other impurities resulting from the synthesis process. The location of the double bond is not limited. The olefin feed composition may comprise α-olefins, internal olefins, or a mixture thereof.

Chevron Alpha Olefin product series (trademark of and sold by Chevron Chemical Co.), manufactures predominantly linear olefins by the cracking of paraffin wax. Commercial olefin products manufactured by ethylene oligomerization are marketed in the United States by Shell Chemical Company under the trademark NEODENE and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121. While most of such olefin products are comprised largely of alpha-olefins, higher linear internal olefins are also commercially produced, for example, by the chlorination-dehydro-chlorination of paraffins, by paraffin dehydrogenation, and by isomerization of alpha-olefins. Linear internal olefin products in the $C_8$ to $C_{22}$ range are marketed by Shell Chemical Company and by Liquichemica Company.

Skeletal isomerisation of linear olefins may be carried out by any known means. Preferably herein, skeletal isomerisation is carried out using the process of U.S. Pat. No. 5,849,960, with use of a catalytic isomerisation furnace. Preferably an isomerisation feed as hereinbefore defined is contacted with an isomerisation catalyst which is effective for skeletal isomerising a linear olefin composition into an olefin composition having an average number of branches per molecule chain of at least 0.7. More preferably the catalyst comprises a zeolite having at least one channel with a crystallographic free channel diameter ranging from greater than 4.2 Angstrom and less than 7 Angstrom, measured at room temperature, with essentially no channel present which has a free channel diameter which is greater than 7 Angstrom.

Suitable zeolites are described in U.S. Pat. No. 5,510,306, the contents of which are incorporated herein by reference, and are described in the Atlas of Zeolite Structure Types by W. M. Meier and D. H. Olson. Preferred catalysts include ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, SUZ-4A, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite, and their isotypic structures. Combinations of zeolites can also be used herein. These combinations can include pellets of mixed zeolites and stacked bed arrangements of catalyst such as, for example, ZSM-22 and/or ZSM-23 over ferrierite, ferrierite over ZSM-22 and/or ZSM-23, and ZSM-22 over ZSM-23. The stacked catalysts can be of the same shape and/or size or of different shape and/or size such as ⅛ inch trilobes over 1/32 inch cylinders for example. Alternatively natural zeolites may be altered by ion exchange processes to remove or substitute the alkali or alkaline earth metal, thereby introducing larger channel sizes or reducing larger channel sizes. Such zeolites include natural and synthetic ferrierite (can be orthorhombic or monoclinic), Sr-D, FU-9 (EP B-55,529), ISI-6 (U.S. Pat. No. 4,578,259), NU-23 (E.P.A.-103,981), ZSM-35 (U.S. Pat. No. 4,016,245) and ZSM-38 (U.S. Pat. No. 4,375,573). Most preferably the catalyst is ferrierite.

The skeletal isomerisation catalyst is suitably combined with a refractory oxide as binding material in known manner, for example natural clays, such as bentonite, montmorillonite, attapulgite, and kaolin; alumina; silica; silica-alumina; hydrated alumina; titania; zirconia and mixtures thereof. More preferred binders are aluminas, such as pseudoboehmite, gamma and bayerite aluminas. These binders are readily available commercially and are used to manufacture alumina-based catalysts.

The weight ratio of zeolite to binder material suitably ranges from about 10:90 to about 99.5:0.5, preferably from about 75:25 to about 99:1, more preferably from about 80:20 to about 98:2 and most preferably from about 85:15 to about 95:5 (anhydrous basis).

Preferably, the skeletal isomerization catalyst is also prepared with at least one acid selected from mono-carboxylic acids and inorganic acids and at least one organic acid with at least two carboxylic acid groups ("polycarboxylic acid"). Suitable acids include those disclosed in U.S. Pat. No. 5,849,960.

Optionally, coke oxidation promoting metals can be incorporated into the instant catalysts to promote the oxidation of coke in the presence of oxygen at a temperature greater than about 250° C. Suitable coke oxidation promoting materials include those disclosed in U.S. Pat. No. 5,849,960.

In a preferred method, the instant catalysts can be prepared by mixing a mixture of at least one zeolite as herein defined, alumina-containing binder, water, at least one monocarboxylic acid or inorganic acid and at least one polycarboxylic acid in a vessel or a container, forming a pellet of the mixed mixture and calcining the pellets at elevated temperatures. Preparation methods of the catalyst are described in U.S. Pat. No. 5,849,960.

High conversion, high selectivity, and high yields are attained by the process described herein.

The present skeletal isomerization process can be operated at a wide range of conditions. Preferably skeletal isomerisation is conducted at elevated temperature in the range 200° C. to 500° C., more preferably 250 to 350° C., and at pressure ranging from 0.1 atmospheres (10 kPa) to 10 atmospheres (1 MPa), more preferably from 0.5 to 5 atmospheres (50 to 500 kPa). Olefin weight hour space velocity (WHSV) can range from 0.1 to 100 per hour. Preferably, the WHSV is between 0.5 to 50, more preferably between 1 and 40, most preferably between 2 and 30 per hour. At lower WHSV's, it is possible to operate at lower temperatures while achieving high yields of skeletally isomerized branched olefins. At higher WHSV's, the temperature is generally increased in order to maintain the desired conversion and selectivity to the skeletally isomerized branched olefins. Further, optimal selectivities are generally achieved at lower olefin partial pressures mentioned above. For this reason, it is often advantageous to dilute the feed stream with a diluent gas such as nitrogen or hydrogen. Although reducing the olefin partial pressure with a diluent may be beneficial to improve the selectivity of the process, it is not necessary to dilute the olefin stream with a diluent.

If a diluent is used, the molar ratio of olefin to diluent can range from 0.01:1 to 100:1, and is generally within the range of 0.1:1 to 5:1.

Although in the present invention, skeletal isomerization is preferred, branching can also be achieved by dimerization.

Broadly speaking, a primary alcohol component is obtained by dimerizing an olefin feed comprising C6-C10 linear olefins in the presence of a dimerization catalyst under dimerization conditions to obtain C12-C20 olefins. Details of suitable dimerisation processes, including process conditions, olefin feed and suitable catalysts, are to be found in U.S. Pat. No. 5,780,694.

Hydroformylation

The branched, skeletally isomerized or dimerized, olefins are subsequently converted to a primary alcohol component, for example, by hydroformylation. In hydroformylation, the skeletally isomerized olefins are converted to alkanols by reaction with carbon monoxide and hydrogen according to the Oxo process. Most commonly used is the "modified Oxo process", using a phosphine, phosphite, arsine or pyridine ligand modified cobalt or rhodium catalyst, as described in U.S. Pat. Nos. 3,231,621; 3,239, 566; 3,239,569; 3,239,570; 3,239,571; 3,420,898; 3,440,291; 3,448,158; 3,448,157; 3,496,203; and 3,496,204; 3,501,515; and 3,527,818. Methods of production are also described in Kirk Othmer, "Encyclopedia of Chemical Technology" 3rd Ed. vol 16, pages 637-653; "Monohydric Alcohols: Manufacture, Applications and Chemistry", E. J. Wickson, Ed. Am. Chem. Soc. 1981.

Hydroformylation is a term used in the art to denote the reaction of an olefin with CO and H2 to produce an aldehyde/alcohol which has one more carbon atom than the reactant olefin. Frequently, in the art, the term hydroformylation is utilized to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols.

Illustrative catalysts include, but are not necessarily limited to, cobalt hydrocarbonyl catalysts and metal-phosphine ligand catalysts comprising metals, including but not limited to, palladium, cobalt and rhodium. The choice of catalysts determines the various reaction conditions imposed. These conditions can vary widely, depending upon the particular catalysts. For example, temperatures can range from about room temperatures to 300° C. When cobalt carbonyl catalysts are used, which are also the ones typically used, temperatures will range from 150° to 250° C. One of ordinary skill in the art, by referring to the above-cited references, or any of the well-known literature on oxo alcohols can readily determine those conditions of temperature and pressure that will be needed to hydroformylate the isomerized or dimerized olefins.

Typical reaction conditions, however, are moderate. Temperatures in the range of 125° C. to 200° C. are recommended. Reaction pressures in the range of 2170 to 10440 kPa are typical, but lower or higher pressures may be selected. Ratios of catalyst to olefin ranging from 1:1000 to 1:1 are suitable.

The ratio of hydrogen to carbon monoxide can vary widely, but is usually in the range of 1 to 10, preferably about 2 moles of hydrogen to one mole of carbon monoxide to favor the alcohol product.

The hydroformylation process can be carried out in the presence of an inert solvent, although it is not necessary. A variety of solvents can be applied such as ketones, e.g. acetone, methyl ethyl ketone, methyl iso-butyl ketone, acetophenone and cyclohexanone; aromatic compounds such as benzene, toluene and the xylenes; halogenated aromatic compounds such as chlorobenzene and orthodichlorobenzene; halogenated paraffinic hydrocarbons such as methylene chloride and carbon tetrachloride; paraffins such as hexane, heptane, methylcyclohexane and isooctane and nitriles such as benzonitrile and acetonitrile.

With respect to the catalyst ligand, mention may be made of tertiary organo phosphines, such as trialkyl phosphines, triamyl phosphine, trihexyl phosphine, dimethyl ethyl phosphine, diamylethyl phosphine, tricyclopentyl(or hexyl) phosphine, diphenyl butyl phosphine, diphenyl benzyl phosphine, triethoxy phosphine, butyl diethyoxy phosphine, triphenyl phosphine, dimethyl phenyl phosphine, methyl diphenyl phosphine, dimethyl propyl phosphine, the tritolyl phosphines and the corresponding arsines and stibines.

Included as bidentate-type ligands are tetramethyl diphdsphinoethane, tetramethyl diphosphinopropane, tetraethyl diphosphinoethane, tetrabutyl diphosphinoethane, dimethyl diethyl diphosphinoethane, tetraphenyl diphosphinoethane, tetraperfluorophenyl diphosphinoethane, tetraphenyl diphosphinopropane, tetraphenyl diphosphinobutane, dimethyl diphenyl diphosphinoethane, diethyl diphenyl diphosphinopropane and tetratrolyl diphosphinoethane.

Examples of other suitable ligands are the phosphabicyclohydrocarbons, such as 9-hydrocarbyl-9-phosphabicyclononane in which the smallest P-containing ring contains at least 5 carbon atoms. Some examples include 9-aryl-9-phosphabicyclo[4.2.1]nonane, (di)alkyl-9-aryl-9-phosphabicyclo[4.2.1]nonane, 9-alkyl-9-phosphabicyclo[4.2.1]nonane, 9-cycloalkyl-9-phosphabicyclo[4.2.1]nonane, 9-cycloalkenyl-9-phosphabicyclo[4.2.1]nonane, and their [3.3.1] and [3.2.1] counterparts, as well as their triene counterparts.

Ethoxylation

The branched primary alcohol composition used to prepare the branched ester composition of the present invention may optionally comprise up to 3 moles of alkylene oxide per mole of alcohol. The upper limit on the number of moles of alkylene oxide reflects the fact that the ester composition of the present invention should not act as a surfactant.

Suitable oxyalkylated alcohols can be prepared by adding to the alcohol or mixture of alcohols to be oxyalkylated a calculated amount, e.g., from about 0.1% by weight to about 0.6% by weight, preferably from about 0.1% by weight to about 0.4% by weight, based on total alcohol, of a strong base, typically an alkali metal or alkaline earth metal hydroxide such as sodium hydroxide or potassium hydroxide, which serves as a catalyst for oxyalkylation. The resulting mixture is dried, as by vapour phase removal of any water present, and an amount of alkylene oxide calculated to provide from about 1 mole to about 3 moles of alkylene oxide per mole of alcohol is then introduced and the resulting mixture is allowed to react until the alkylene oxide is consumed, the course of the reaction being followed by the decrease in reaction pressure.

Further details of suitable oxyalkylation processes including process conditions can be found in U.S. Pat. No. 6,150,322.

Other suitable alkoxylation catalysts for use herein include rare earth phosphates, e.g. lanthanum phosphate and barium phosphate, described in WO02/47817 and double metal cyanide catalysts such as those described in co-pending U.S. patent application Ser. No. 60/485,429.

Suitable alkylene oxides for use herein include ethylene oxide, propylene oxide and butylene oxide, and mixtures thereof, preferably ethylene oxide.

Esterification Process

The branched ester composition of the present invention is obtainable by reaction of a carboxylic acid with a branched alcohol composition under esterification reaction conditions.

Any esterification catalyst is suitable for use herein. Suitable esterification catalysts are listed in Vogel's Textbook of practical organic chemistry, Fifth Ed., 1989, revised by B. S. Furniss et al, Longman Scientific & Technical, Harlow, Essex, England; copublished in the United States with John Wiley & Sons, Inc., New York, 1989, pages 695-707.

Examples of suitable esterification catalysts for use herein, include, but are not limited to, hydrochloric acid, sulphuric acid, p-toluenesulphonic acid and cation exchangers.

A particularly preferred esterification catalyst for use herein is a strongly acidic cation exchange resin commercially available from BDH Chemicals, Poole, England, under the tradename Amberlyst 15.

The catalyst is used herein in an amount in the range from 0.05% to 5% by weight of the esterification reaction mixture.

The esterification reaction is preferably carried out at a temperature in the range of from 0° C. to 250° C., more preferably from 50° C. to 200° C., even more preferably from 75° C. to 175° C. at pressures from 0.1 to 2 bar(a), preferably at atmospheric pressure.

The esterification reaction of a carboxylic acid and a particular branched alcohol composition as described herein produces a particular branched ester composition. Hence according to another aspect of the present invention there is provided a branched ester composition comprising at least one ester compound of formula RCOOR' wherein R is a carbon chain derived from a carboxylic acid as described hereinabove and R' is a carbon chain derived from a primary alcohol as described hereinabove.

In a preferred embodiment herein, the branched ester composition of the present invention comprises at least one ester compound of formula RCOOR' wherein R is a straight chain or branched, substituted or unsubstituted, alkyl or alkenyl group having from 1 to 30 carbon atoms or a substituted or unsubstituted cycloaromatic group having from 6 to 14 carbon atoms and wherein R' is an alkyl or alkenyl group having from 8 to 36 carbon atoms wherein said R' group has an average number of branches per molecule of from 0.7 to 3.0, said branching on the R' group comprising methyl and ethyl branches.

In a preferred embodiment, the branched ester composition of the present invention comprises at least one ester compound of formula RCOOR' wherein R is a straight chain alkyl group having from 10 to 22 carbon atoms.

In another preferred embodiment, the branched ester composition of the present invention comprises at least one ester compound of formula RCOOR' wherein R is a cycloaromatic group, especially a cycloaromatic group having 6 carbon atoms in the aromatic ring.

In another preferred embodiment, the branched ester composition of the present invention comprises at least one ester compound of formula RCOOR' wherein R' is an alkyl group having from 8 to 36 carbon atoms, preferably from 11 to 21 carbon atoms (exclusive of any alkylene oxide groups).

In yet another preferred embodiment, the branched ester composition of the present invention comprises at least one ester compound of formula RCOOR' wherein R' is an alkyl group having an average number of branches per molecule of 1.0 to 3.0, preferably 1.5 to 2.3, especially from 1.7 to 2.1.

Personal Care Compositions

The personal care compositions of the present invention comprise a safe and effective amount of the branched ester compound. Suitably the personal care compositions of the present invention comprise from 0.01 to 30%, preferably from 0.1 to 20%, more preferably from 0.5% to 15% and especially from 1% to about 10% by weight of the branched ester compound.

Cosmetically-Acceptable Vehicle

The personal care compositions herein also comprise a cosmetically-acceptable vehicle in addition to the branched ester component. The cosmetically-acceptable vehicle is generally present in a safe and effective amount, preferably from 1% to 99.99%, more preferably from about 20% to about 99%, especially from about 60% to about 90%. The cosmetically-acceptable vehicle can contain a variety of components suitable for rendering such compositions cosmetically, aesthetically or otherwise, acceptable or to provide them with additional usage benefits. The components of the cosmetically-acceptable vehicle should be physically and chemically compatible with the branched ester component and should not unduly impair the stability, efficacy or other benefits associated with the personal care compositions of the invention.

Suitable ingredients for inclusion in the cosmetically-acceptable vehicle are well known to those skilled in the art. These include, but are not limited to, emollients, oil absorbents, antimicrobial agents, binders, buffering agents, denaturants, cosmetic astringents, film formers, humectants, surfactants, emulsifiers, sunscreen agents, oils such as vegetable oils, mineral oil and silicone oils, opacifying agents, perfumes, colouring agents, pigments, skin soothing and healing agents, preservatives, propellants, skin penetration enhancers, solvents, suspending agents, emulsifiers, cleansing agents, thickening agents, solubilising agents, waxes, inorganic sunblocks, sunless tanning agents, antioxidants and/or free radical scavengers, chelating agents, suspending agents, sunless tanning agents, antioxidants and/or radical scavengers, anti-acne agents, anti-dandruff agents, anti-inflammatory agents, exfolients/desquamation agents, organic hydroxy acids, vitamins, natural extracts, inorganic particulates such as silica and boron nitride, deodorants and antiperspirants.

Non limiting examples of such materials are described in Harry's Cosmeticology, $7^{th}$ Edition., Harry & Wilkinson (Hill Publishers, London 1982); in The Chemistry and Manufacture of Cosmetics, $2^{nd}$. Edition., deNavarre (Van Nostrand 1962-1965); and in the Handbook of Cosmetic Science and Technology, $1^{st}$ Edition., Knowlton & Pearce (Elsevier 1993); CTFA International Cosmetic Ingredient Dictionary and Handbook, $7^{th}$ Edition, volume 2, edited by Wenniger and McEwen (The Cosmetic, Toiletry, and Fragrance Association, Inc., Washington, D.C., 1997); and WO01/89466.

Preferred compositions have an apparent viscosity of from 5,000 to about 2,000,000 mPa.s, measured using a Brookfield DVII RV viscometer, spindle TD, at 5 rpm, 25° C. and ambient pressure. The viscosity will vary depending on whether the composition is a cream or lotion.

Compositions of the present invention are preferably aqueous, and more preferably are in the form of an emulsion, such as an oil-in-water or water-in-oil emulsion. For example, in the case of an oil-in-water emulsion a hydrophobic phase containing an oily material is dispersed within an aqueous phase. Oil-in-water emulsions typically comprise from 1% to 50%, preferably from 1% to 30% by weight of the dispersed hydrophobic phase and from 1% to about 99%, more preferably from 40% to about 90% by weight of the continuous aqueous phase. The emulsion may also comprise a gel network, such as described in G. M. Eccelston, Application of Emulsion Stability Theories to Mobile and Semisolid O/W Emulsions, Cosmetic & Toiletries, Vol. 101, November 1996, pp. 73-92.

The compositions of the invention will preferably be formulated to have a pH of from about 4.5 to about 9, more preferably from about 5 to about 8.5.

The compositions herein can be formulated into a wide variety of product forms such as are known in the art and can be used for a wide variety of purposes. Suitable product forms include, but are not limited to, lotions, creams, gels, sticks, sprays, ointments, pastes and mousses.

The compositions of the present invention can be formulated into either non-cleansing or cleansing formulations. Examples of non-cleansing formulations include hair conditioners, skin moisturizing creams, sunscreen compositions, night creams, antiperspirants, lipsticks, cosmetic foundations, body lotions, and the like. Examples of cleansing formulations include shampoos, facial cleansers, shower gels, bath foams, hand cleansers, and the like. Generally, cleansing formulations contain relatively high levels of surfactants, generally greater than 5%, preferably greater than 10%.

In preferred embodiments herein the personal care compositions are formulated as non-cleansing formulations, preferably comprising 5% or less, more preferably 3% of less, by weight, of surfactant.

Any surfactant known for use in personal care compositions can be used herein, provided that the selected agent is chemically and physically compatible with other ingredients in the composition. Suitable surfactants for use in the compositions herein include nonionic, anionic, amphoteric, zwitterionic and cationic surfactants, such as those described in WO01/89466.

Preferred cosmetically-acceptable vehicles herein contain a hydrophilic diluent, typically at a level of 60% to 99% by weight of composition. Suitable hydrophilic diluents include water, low molecular weight monohydric alcohols, glycols and polyols, including propylene glycol, polypropylene glycol, glycerol, butylene glycol, sorbitol esters, ethanol, isopropanol, ethoxylated ethers, propoxylated ethers and mixtures thereof. A preferred diluent is water.

The cosmetically-acceptable vehicle herein may contain an emulsifier to help disperse and suspend the discontinuous phase within the continuous aqueous phase. An example of a suitable emulsifier is PEG-30 dihydroxystearate commercially available from Uniquema Americas and a mixture of glyceryl Stearate and PEG-100 stearate commercially available under the tradename Lipomulse 165 from Lipo Chemicals, Inc.

Preferred compositions herein comprise emollient materials, in addition to the branched ester component which itself has emolliency properties. Emollients are materials which lubricate the skin, increase the softness and smoothness of the skin, prevent or relieve dryness, and/or protect the skin. Emollients are typically oily or waxy materials which are water-immiscible. In an oil-in-water emulsion, emollients therefore generally form part of the disperse oil phase. Suitable emollients are described in Sagarin, Cosmetics, Science and Technology, $2^{nd}$ Edition, Vol. 1, pp. 32-43 (1972) and in WO01/89466.

Examples of preferred emollients include those disclosed in WO01/89466 such as straight and branched chain hydrocarbons having from 7 to 40 carbon atoms, such as dodecane, squalane, cholesterol, isohexadecane and the $C_7$-$C_{40}$ isoparaffins, $C_1$-$C_{30}$ alcohol esters of $C_1$-$C_{30}$ carboxylic acids and of $C_2$-$C_{30}$ dicarboxylic acids such as isononyl isononanoate, isopropyl myristate, myristyl propionate, isopropyl stearate, isopropyl isostearate, methyl isostearate, behenyl behenate, octyl palmitate, dioctyl maleate, diisopropyl adipate, and diisopropyl dilinoleate, $C_1$-$C_{30}$ mono- and poly-esters of sugars and related materials such as those disclosed in WO01/89466; and vegetable oils and hydrogenated vegetable oils including safflower oil, castor oil, coconut oil, cottonseed oil, palm kernal oil, palm oil, peanut oil, soybean oil, rapeseed oil, linseed oil, rice bran oil, pine oil, sesame oil, sunflower seed oil, partially and fully hydrogenated oils of the above, and mixtures thereof.

Preferred compositions herein contain silicone-based ingredients such as volatile or non-volatile organopolysiloxane oils. Preferred for use herein are organopolysiloxanes selected from polyalkylsiloxanes, alkyl substituted dimethicones, dimethiconols, polyalkylaryl siloxanes and cyclomethicones, preferably polyalkylsiloxanes and cyclomethicones. Also useful herein are silicone-based emulisifers such as dimethicone copolyols, an example of which is cetyl dimethicone copolyol, supplied by Goldschmidt under the tradename Abil EM90.

The compositions herein preferably comprise a thickening agent such as those described in WO01/89466. Suitable thickening agents include carboxylic acid polymers, crosslinked polacrylates, polyacrylamides, xanthan gum, cellulose derivatives, and mixtures thereof. Examples of suitable thickening agents include the Carbopol series of materials commercially available from B.F. Goodrich and cetyl hydroxymethyl cellulose supplied by Hercules Aqualon under the tradename Natrosol 250 HR CS.

Preferred compositions herein comprise a humectant at a level of about 5% to about 30% by weight. Preferred humectants include, but are not limited to, glycerine, polyoxyalkylene gycol, urea, D or DL panthenol and alkylene glycols such as propylene glycol or butylene glycol.

When it is desired to provide protection from the harmful effects of the sun, the compositions herein can contain a safe and effective amount of one or more sunscreen ingredients, selected from inorganic or organic sunscreens. Suitable sunscreens include those disclosed in WO01/89466.

The compositions herein may comprise a long chain alcohol. Suitable long chain alcohols can be selected from linear or branched, saturated or unsaturated alcohols having an average number of carbon atoms in the range of from 8 to 36.

Examples of naturally derived long chain alcohols include the fatty alcohols cetyl alcohol, stearyl alcohol and behenyl alcohol.

Other suitable long chain alcohols include those commercially available from The Shell Chemical Company under the tradename NEODOL. Examples of NEODOL alcohols include NEODOL 23, NEODOL 91, NEODOL 1, NEODOL 45 and NEODOL 25. All of these alcohols are predominantly linear alcohols.

Other suitable long chains alcohols include the branched primary alcohols as disclosed and prepared in U.S. Pat. No. 5,849,960.

Other suitable alcohols include alcohols of the SAFOL series such as SAFOL 23, alcohols of the LIAL series such LIAL 123, and alcohols of the ALFONIC series, all of which are commercially available from Sasol.

Also suitable for use herein are the so-called "Guerbet" alcohols, for example, EUTANOL G16, commercially available from Cognis Corporation.

The compositions herein can be prepared according to procedures usually used in cosmetics and that are well known and understood by those skilled in the art.

The following examples will illustrate the nature of the invention, but are not intending to be limiting in any way.

EXAMPLE 1

Preparation of a Stearate Ester Composition

The preparation of the ester composition was carried out in xylene (118.7 g) with an excess of NEODOL 67 (104.3 g), an alcohol composition having an average of 16.5 carbon atoms per molecule and commercially available from The Shell Chemical Company, over stearic acid (81.7 g) commercially available from Aldrich having a purity of 95% wt. The reaction was acid catalyzed using either 2.8 g of a strongly acidic cation exchange resin commercially available from BDH Chemicals, Poole, England under the tradename Amberlyst 15.

All materials were directly weighed into a glass 3-necked round-bottomed flask equipped with a magnetic stirrer, a reflux condenser, a nitrogen inlet and a Dean and Stark set-up. The mixture was heated to 150° C. under nitrogen by means of an electrical jacket to a gentle reflux. The water formed during the reaction was removed by the Dean and Stark set-up (a water-trap). The esterification reaction was complete within 3 hours of refluxing, as measured by the amount of water removed.

After complete esterification, the acidic resin was removed by filtration at 50-60° C. and was treated with a neutral/basic $Al_2O_3$ extrudate (commercially available under the tradename AX-200 from Criterion) to neutralize and adsorb contaminants. The alumina was filtered off at 50-60° C. after at least 2 hours of stirring.

The stearate ester product was purified as follows. Most of the xylene solvent was removed by means of a rotary evaporator at 75° C. and 16-6 mbar. The remainder of the xylene solvent and the excess of the branched alcohol composition, NEODOL 67 alcohol, (having a boiling point of 317° C.) were removed by evaporation using a laboratory wiped film evaporator at 170° C. and 0.03 mbar. The final ester product was an off-white semi-solid liquid at room temperature. NMR spectroscopy indicated that the ester product contained small amounts (<1% wt) of xylene. Unlike the use of p-TSA as catalyst in Example 4 below, the ester yield using the acidic resin was almost quantitative (142.2 g ester; 96% of the theoretical yield).

EXAMPLE 2

Example 1 was repeated twice except at three times the scale. Similar results to those of Example 1 were obtained.

EXAMPLE 3

Example 1 was repeated using p-toluenesulphonic acid monohydrate (hereinafter "p-TSA") as the esterification catalyst. p-TSA having a purity of 97% wt is commercially available from Baker Chemicals. 3.0 g of p-TSA was used in 117.4 g of xylene, 105.3 g of NEODOL 67, the alcohol composition used in Example 1 and 79.2 g stearic acid.

In the case of p-TSA, the resulting ester solution was extracted twice with a 1M $Na_2CO_3$ solution, followed by one wash with demineralised water to remove the p-TSA. The resulting solution was dried over $Mg_2SO_4$ which was filtered off afterwards. NMR indicated the presence of traces (<0.2% wt) of the Na-salt of p-TSA in the purified ester.

With the use of p-TSA, the ester yield was 107.0 g (75% of the theoretical yield).

Solubility Experiments

The ester product prepared according to Example 1 was mixed with various solvents commonly found in personal care formulations in 90/10, 50/50 and 10/90 weight ratios as indicated in Tables 1-6 below. Solubility measurements were made at both room temperature and 65° C. For comparison, the same measurements were conducted on two commercial isocetyl stearates based on Guerbet-type branched alcohols. As a further comparison solubility measurements at 50/50 and 10/90 weight ratios were also made using a commercial linear cetearyl stearate. These solubility results are shown in Tables 1-6 below.

TABLE 1

90% wt Ester/10% wt Solvent, except where noted otherwise, at 23° C. (4.5 grams of ester/0.5 grams of solvent)

| | Isocetyl Stearate[a] | Ceraphyl 494[b] | Ester prepared according to Example 1 |
|---|---|---|---|
| Castor Oil | 1 Phase, miscible | 1 Phase, miscible | 2 Phase, 5 mm top layer, bottom layer cloudy |
| Propylene Glycol | 2 Phase, 4 mm bottom layer | 2 Phase, 3 mm bottom layer, cloudy top | 2 Phase, 8 mm clear top layer; bottom layer cloudy |
| Dimethylsiloxane | 2 Phase, 2 mm clear bottom layer, top layer cloudy | 2 Phase, 2 mm clear bottom layer, top layer cloudy | 2 Phase, 6 mm clear top layer, bottom layer cloudy |
| Ethanol | 2 Phase, 3 mm clear top layer, bottom layer cloudy | 2 Phase, 2 mm top layer, bottom layer cloudy | one phase, cloudy |
| Glycerine | 2 Phase, 3 mm clear bottom layer, top layer cloudy | 2 Phase, 3 mm clear bottom layer, top layer cloudy | 2 Phase, 3 mm clear bottom layer, top layer cloudy |
| Mineral Oil | Miscible, 1 Phase, clear | Miscible, 1 Phase, clear | 2 phase, cloudy |
| Stearic Acid | All crystal solid | All crystal solid | Flowable cloudy liquid |
| Stearyl Alcohol | All crystal solid | All crystal solid | All crystal solid[1] |
| Water | 2 Phase cloudy top layer, 3 mm clear bottom layer | 2 Phase cloudy top layer, 3 mm clear bottom layer | 2-phase, 3 mm clear bottom layer |

[a]Isocetyl stearate commercially available from A.&.E. Connock, Fordingbridge, England
[b]Ceraphyl 494 is an isocetyl stearate commercially available from ISP, Inc., Wayne, New Jersy, USA.
[1]Ratio of 89% wt (ester)/11% wt (solvent) (4.501 grams of ester/0.566 grams of solvent)

TABLE 2

90% wt Ester/10% wt Solvent, except where noted otherwise, at 65° C. (4.5 grams of ester/0.5 grams of solvent)

| | Isocetyl Stearate[a] | Ceraphyl 494[b] | Ester prepared according to Example 1 |
|---|---|---|---|
| Castor Oil | 1 Phase, miscible, clear | 1 Phase, miscible, clear | 1 Phase, miscible, clear, yellow tinge to solution |
| Propylene Glycol | 2 Phase, clear top layer, 5 mm clear bottom layer | 2 Phase, cloudy top layer, 4 mm clear bottom layer | 2 Phase, 5 mm cloudy bottom layer; cloudy yellow top layer |
| Dimethylsiloxane | 1 Phase, miscible, cloudy | 1 Phase, clear | 2 Phase, 2 mm cloudy bottom layer; cloudy yellow top layer |
| Ethanol | Cloudy 1 Phase | 1 Phase, cloudy, some solids entrained in solution | 1 Phase, cloudy, yellow solution |
| Glycerine | 2 Phase, 3 mm clear bottom layer, clear top layer | 3 Phase, 2 mm clear bottom layer, 1 mm cloudy middle layer, cloudy top layer | 2 Phase, 5 mm clear bottom layer, cloudy yellow top layer |
| Mineral Oil | 1 Phase, clear, Miscible, | 1 Phase, clear, miscible | 1 phase, clear, slightly yellow |
| Stearic Acid | Miscible, 1 Phase, clear | Miscible, 1 Phase, clear | Miscible, 1 Phase, clear |
| Stearyl Alcohol | Miscible, 1 Phase, clear | Miscible, 1 Phase, clear | Miscible, 1 Phase, clear[1] |
| Water | 2 Phase, 5 mm clear bottom layer, cloudy top layer | 2 Phase, 5 mm clear bottom layer, cloudy top layer | 2 Phase, 5 mm clear bottom layer, cloudy yellow top layer |

[a] Isocetyl stearate commercially available from A.&.E. Connock, Fordingbridge, England
[b] Ceraphyl 494 is an isocetyl stearate commercially available from ISP, Inc., Wayne, New Jersy, USA.
[1] Ratio of 89% wt (ester)/11% wt (solvent) (4.501 grams of ester/0.566 grams of solvent)

TABLE 3

50% wt Ester/50% wt Solvent (4.5 grams ester/4.5 grams solvent), except where stated otherwise, at 23.5° C.

| | Isocetyl Stearate[a] | Ceraphyl 494[b] | Cetearyl Stearate[c] | Ester prepared according to Example 1 |
|---|---|---|---|---|
| Castor Oil | 1 Phase, clear, miscible | 1 Phase, clear, miscible | White crystalline solid | 1 Phase, clear, miscible |
| Propylene Glycol | 2 Phase, 30 mm clear bottom layer, 37 mm cloudy top layer | 2 Phase, 35 mm clear bottom layer, 37 mm cloudy top layer[2] | White crystalline solid | 2 Phase, 42 mm cloudy yellow bottom layer; 20 mm semi-clear yellow top layer |
| Dimethylsiloxane | 2 Phase, 32 mm clear bottom layer, 38 mm cloudy top layer | 2 Phase, 32 mm clear cottom layer, 38 mm cloudy top layer | White crystalline solid | 3 Phase, 16 mm semi-clear bottom layer, 50 mm cloudy middle layer, 5 mm clear top layer |
| Ethanol | 2 Phase, 38 mm clear bottom layer, 37 mm clear top layer | 2 Phase, 40 mm cloudy bottom layer, 38 mm clear top layer | White crystalline solid | 3 Phase, 13 mm cloudy bottom layer, 32 mm semi-cloudy middle layer, 34 mm clear top layer |
| Glycerine | 2 Phase, 25 mm semi-clear bottom layer, 37 mm clear top layer | 3 Phase, 22 mm semi-clear bottom layer, 4 mm emulsion middle layer, 30 mm clear top layer with drops | White crystalline solid | 3 Phase, 19 mm clear bottom layer, 37 mm cloudy yellow middle layer, 5 mm clear top layer |
| Mineral Oil | 1 Phase, clear, Miscible, | 1 Phase, clear, miscible | White crystalline solid | 2 phase, 54 mm cloudy bottom layer, 20 mm clear top layer |
| Stearic Acid | Crystal solid throughout | Crystal solid throughout | White crystalline solid | Crystal solid throughout |
| Stearyl Alcohol | Crystal solid throughout | Crystal solid throughout | White crystalline solid | Crystal solid throughout[3] |
| Water | 2 Phase, 31 mm clear bottom layer, 37 mm cloudy top layer | 3 Phase, 22 mm clear bottom layer, 20 mm large emulsion, 28 mm cloudy top layer | 2 phase, 31 mm clear bottom, white solid top layer | 3 Phase, 10 mm clear bottom layer, 43 mm cloudy yellow middle layer, 25 mm semi-clear top layer |

[a] Isocetyl stearate commercially available from A.&.E. Connock, Fordingbridge, England
[b] Ceraphyl 494 is an isocetyl stearate commercially available from ISP, Inc., Wayne, New Jersy, USA.
[c] Linear cetearyl stearate commercially available from A.&E. Connock, Fordingbridge, England
[2] 46% wt Ester/54% wt solvent (4.527 grams ester/5.230)
[3] 51% wt ester/49% wt solvent (4.501 grams ester/4.406 grams solvent)

TABLE 4

50% Ester/50% Solvent (4.5 grams ester/4.5 grams solvent), except where noted otherwise, at 65° C.

|  | Isocetyl Stearate[a] | Ceraphyl 494[b] | Cetearyl Stearate[c] | Ester prepared according to Example 1 |
|---|---|---|---|---|
| Castor Oil | 1 Phase, miscible, clear | 1 Phase, miscible, clear | 1 phase, clear, miscible | 1 Phase, clear, miscible |
| Propylene Glycol | 2 Phase, 31 mm clear bottom layer, 38 mm clear top layer | 2 Phase, 35 mm clear bottom layer, 33 mm clear top layer[2] | 2 Phase, 31 mm clear bottom, 38 mm clear top layer | 2 Phase, 31 mm clear bottom layer; 37 mm semi-clear yellow top layer |
| Dimethyl-siloxane | 2 Phase, 35 mm clear bottom layer, 35 mm clear top layer | 2 Phase, 35 mm clear bottom layer, 35 mm clear top layer | 2 Phase, 34 mm clear bottom layer, 38 mm clear top layer | 2 Phase, 35 mm clear bottom layer; 37 mm cloudy top layer |
| Ethanol | 2 Phase, 42 mm cloudy bottom layer, 35 mm clear top layer | 2 Phase, 43 mm cloudy bottom layer, 37 mm clear top layer | 2 Phase, 42 mm clear bottom layer, 36 mm cloudy top layer | 2 Phase, 42 mm yellow bottom layer, 35 mm cloudy top layer |
| Glycerine | 2 Phase, 25 mm clear bottom layer, 37 mm semi-cloudy top layer | 3 Phase, 20 mm clear bottom layer, 5 mm emulsion (Lg), 37 mm semi-cloudy top layer | 2 Phase, 24 mm clear bottom layer, 38 mm cloudy top layer | 2 Phase, 24 mm clear bottom layer, 37 mm cloudy top layer |
| Mineral Oil | 1 Phase, clear, Miscible, | 1 Phase, clear, miscible | 1 Phase, clear, miscible | 1 phase, clear, miscible |
| Stearic Acid | Miscible, 1 Phase, clear | Miscible, 1 Phase, clear | Miscible, 1 phase, clear | Miscible, 1 Phase, clear |
| Stearyl Alcohol | Miscible, 1 Phase, clear | Miscible, 1 Phase, clear | Miscible, 1 Phase, clear | Miscible, 1 Phase, clear[3] |
| Water | 2 Phase, 33 mm clear bottom layer, 40 mm cloudy top layer | 3 Phase, 30 mm semi-clear bottom layer, 13 mm cloudy middle layer, 26 mm cloudy top layer | 2 Phase, 31 mm clear bottom layer, 37 mm cloudy top layer | 2 Phase, 31 mm clear bottom layer, 39 mm cloudy yellow top layer |

[a] Isocetyl stearate commercially available from A.&.E. Connock, Fordingbridge, England
[b] Ceraphyl 494 is an isocetyl stearate commercially available from ISP, Inc., Wayne, New Jersy, USA.
[c] Linear cetearyl stearate commercially available from A.&.E. Connock, Fordingbridge, England
[2] 46% wt Ester/54% wt solvent (4.527 grams ester/5.230 grams solvent)
[3] 51% wt ester/49% wt solvent (4.501 grams ester/4.406 grams solvent)

TABLE 5

10% Ester/90% Solvent (0.5 grams ester/0.45 grams solvent), except where noted otherwise, at 23.5° C.

| | Isocetyl Stearate[a] | Ceraphyl 494[b] | Cetearyl Stearate[c] | Ester prepared according to Example 1 |
|---|---|---|---|---|
| Castor Oil | 1 Phase, miscible, clear[d] | 1 Phase, miscible, clear | Cloudy solid | 1 Phase, cloudy[e] |
| Propylene Glycol | 2 Phase, 30 mm clear bottom layer, 5 mm cloudy bottom layer (should one of these say top) | 3 Phase, 31 mm clear bottom layer, 4 mm clear middle layer, 2 mm clear top layer | Cloudy liquid | 2 Phase, 31 mm clear bottom layer, 6 mm cloudy top layer |
| Dimethyl-siloxane | 1 Phase, clear, miscible | 1 Phase, clear, miscible | White solid | 2 Phase, 6 mm clear bottom layer; 31 mm cloudy top layer |
| Ethanol | 2 Phase, 5 mm clear bottom layer, 37 mm clear top layer | 2 Phase, 5 mm clear bottom layer, 38 mm clear top layer | Cloudy liquid | 2 Phase, 5 mm cloudy bottom layer, 37 mm clear top layer |
| Glycerine | 2 Phase, 26 mm clear bottom layer, 5 mm clear top layer | 2 Phase, 26 mm clear bottom layer, 7 mm clear top layer | Cloudy liquid | 2 Phase, 25 mm clear bottom layer, 5 mm cloudy top layer |
| Mineral Oil | 1 Phase, clear, Miscible | 1 Phase, clear, miscible | Cloudy solid | 1 phase, semi-clear |
| Stearic Acid | All crystals | All crystals | White crystalline solid | All crystals |
| Stearyl Alcohol | All crystals | All crystals | White crystalline solid | All crystals |
| Water | 2 Phase, 33 mm clear bottom layer, 4 mm clear top layer | 2 Phase, 22 mm clear bottom layer, 5 mm clear top layer | 33 mm clear bottom layer, 5 mm white solid top layer | 2 Phase, 30 mm clear bottom layer, 6 mm cloudy top layer |

[a] Isocetyl stearate commercially available from A.&E. Connock, Fordingbridge, England
[b] Ceraphyl 494 is an isocetyl stearate commercially available from ISP, Inc., Wayne, New Jersy, USA.
[c] Linear cetearyl stearate commercially available from A.&E. Connock, Fordingbridge, England
[d] 11% wt ester/89% wt solvent (0.562 grams ester/4.536 grams solvent)
[e] 8% wt ester/92% wt solvent (0.504 grams ester/5.515 grams solvent)

TABLE 6

10% Ester/90% Solvent (0.5 grams ester/4.5 grams solvent), except where noted otherwise, at 65° C.

| | Isocetyl Stearate[a] | Ceraphyl 494[b] | Cetearyl Stearate[c] | Ester prepared according to Example 1 |
|---|---|---|---|---|
| Castor Oil | 1 Phase, miscible, clear[d] | 1 Phase, miscible, clear | 1 Phase, miscible, clear | 1 Phase, miscible, clear[e] |
| Propylene Glycol | 2 Phase, 32 mm clear bottom layer, 5 mm clear top layer | 2 Phase, 32 mm clear bottom layer, 5 mm cloudy top layer | 2 Phase, 31 mm clear bottom layer, 5 mm clear top layer | 2 Phase, 32 mm clear bottom layer; 5 mm clear top layer |
| Dimethyl-siloxane | 1 Phase, clear, miscible | 1 Phase, clear, miscible | 1 Phase, clear, miscible | 1 Phase, clear, miscible |
| Ethanol | 2 Phase, 3 mm cloudy bottom layer, 42 mm semi-clear top layer | 2 Phase, 3 mm clear Layer, 41 mm cloudy spotty top layer | 2 Phase, 5 mm clear bottom layer, 41 mm cloudy bottom layer | 2 Phase, 3 mm cloudy bottom layer, 42 mm clear top layer |
| Glycerine | 2 Phase, 27 mm clear bottom layer, 5 mm clear top layer | 2 Phase, 26 mm clear bottom layer, 6 mm clear top layer | 2 Phase, 24 mm clear bottom layer, 5 mm clear bottom layer | 2 Phase, 26 mm clear bottom layer, 5 mm clear top layer |
| Mineral Oil | 1 Phase, clear, Miscible, | 1 Phase, clear, miscible | 1 Phase, clear, miscible | 1 phase, clear, miscible |
| Stearic Acid | Miscible, 1 Phase, clear | Miscible, 1 Phase, clear | Miscible, 1 Phase, clear | 2 Phase, 33 mm top clear layer, 10 mm cloudy bottom layer cloudy due to crystals |
| Stearyl Alcohol | Miscible, 1 Phase, clear | 2 Phase, 35 mm clear top layer, 10 mm cloudy bottom layer due to crystals | Miscible, 1 Phase, clear | 2 Phase, 35 mm clear top layer, 15 mm cloudy bottom layer due to crystals |
| Water | 2 Phase, 32 mm clear bottom layer, 6 mm clear top layer | 2 Phase, 33 mm clear bottom layer, 6 mm cloudy top layer | 2 Phase, 31 mm clear bottom later, 5 mm cloudy top layer | 2 Phase, 32 mm clear bottom layer, 7 mm clear top layer |

[a] Isocetyl stearate commercially available from A.&E. Connock, Fordingbridge, England
[b] Ceraphyl 494 is an isocetyl stearate commercially available from ISP, Inc., Wayne, New Jersy, USA.
[c] Linear cetearyl stearate commercially available from A.&E. Connock, Fordingbridge, England
[d] 11% wt ester/89% wt solvent (0.562 grams ester/4.536 grams solvent)
[e] 8% wt ester/92% wt solvent (0.504 grams ester/5.515 grams solvent)

The solubility data above show that all four esters exhibit similar solubility characteristics at 65° C. They are fully or partially miscible with the nonpolar solvents including castor oil, mineral oil, dimethyl siloxane, stearic acid, and stearyl alcohol. At the same temperature, they are not miscible with the polar solvents including water, glycerine, ethanol, and propylene glycol. This behaviour correlates with the fact that the esters all have melting point ranges below 65° C. and are therefore clear liquids at 65° C.

In contrast, at room temperature, the linear cetearyl stearate is a waxy solid, the ester prepared according to Example 1 is a solid-liquid slurry, and the two Guerbet alcohol-based commercial esters are fully melted liquids. As a result, the Guerbet alcohol-based esters maintain their solubility in the nonpolar solvents at room temperature while the linear cetearyl stearate ester precipitates as a solid out of solution. Consistent with its intermediate physical property state, the experimental ester prepared according to Example 1 exhibits solubility characteristics in between those of the linear cetearyl alcohol-based ester and the highly branched Guerbet alcohol-based esters.

FORMULATION EXAMPLES

EXAMPLE 4

Night Cream (Water-in-oil Emulsion)

To prepare a night cream in the form of a water-in-oil emulsion having the ingredients shown below, the ingredients of phase A are combined at 75° C., the ingredients of phase B are combined at 50° C. and then phase B is slowly added to phase A. The two phases are mixed until a homogeneous mixture results.

| Phase | Ingredient | Wt % |
| --- | --- | --- |
| A | Abil EM90[1] | 5 |
| A | Arlacel P135[2] | 1 |
| A | Castorwax MP70[3] | 2.5 |
| A | Octyl Palmitate | 5 |
| A | Ester product of any of Examples 1-3 | 15 |
| A | Vitamin E acetate | 0.1 |
| B | Propylene glycol | 2.5 |
| B | Natrosol 250HR CS[4] | 0.8 |
| B | Sodium chloride | 0.75 |
| B | Glydant[5] | 0.2 |
| B | Deionized Water | to 100 |

[1]Cetyl Dimethicone Copolyol supplied by Goldschmidt
[2]PEG-30 Dihydroxystearate supplied by Uniqema Americas
[3]Hydrogenated Castor Oil supplied by CasChem, Inc.
[4]Cetyl Hydroxymethylcellulose supplied by Hercules/Aqualon
[5]DMDM Hydantoin preservative supplied by Lonza Inc.

EXAMPLE 5

Moisturiser (Oil-in-water Emulsion)

An oil-in-water moisturizer having the ingredients shown below can be prepared by combining the ingredients of phase A at 75° C., combining the ingredients of phase B at 75° C. and adding phase B to phase A. Phase C is added to the resulting mixture and cooled to 40° C. Finally Phase D is added.

| Phase | Ingredient | Wt % |
| --- | --- | --- |
| A | Deionised water | to 100 |
| A | Tetrasodium EDTA | 0.1 |
| A | Glycerine | 2.5 |

-continued

| Phase | Ingredient | Wt % |
| --- | --- | --- |
| A | Carbopol 980[6] (2% solution) | 15 |
| B | Ester product of any of Examples 1-3 | 10 |
| B | Lipomulse 165[7] | 2.5 |
| B | Stearic Acid | 2.5 |
| B | Cetearyl Alcohol | 1 |
| B | Dimethicone DC200-50[8] | 1 |
| C | NaOH (20% solution) | 0.77 |
| D | Germaben II[9] | 1 |

[6]Carbomer supplied by B. F. Goodrich
[7]Glyceryl Stearate and PEG 100 Stearate supplied by Lipo Chemicals, Inc.
[8]Supplied by Dow Corning
[9]Propylene Glycol and Diazolidinyl Urea and Methylparaben and Propylparaben preservative supplied by Sutton Laboratories

We claim:

1. A branched primary alcohol carboxylic acid ester composition wherein the branched alcohol group of the composition has from about 8 to about 36 carbon atoms and an average number of branches per molecule of from about 1.0 to about 3.0, said branching comprising methyl and ethyl branches, wherein at least 40 percent of the number of branches in the branched alcohol group are methyl branches and wherein from 5 to 30 percent of the number of branches in the branched alcohol group are ethyl branches.

2. The branched ester composition of claim 1 wherein the branched alcohol group of the composition has an average number of branches per molecule in the range from about 1.5 to about 2.3.

3. The branched ester composition of claim 1 wherein the carboxylic acid group has from about 1 to about 30 carbon atoms.

4. The branched ester composition of claim 1 wherein the carboxylic acid group is selected from straight chain or branched, substituted or unsubstituted, saturated or unsaturated, aliphatic carboxylic acid groups having from about 1 to about 30 carbon atoms, and substituted or unsubstituted cycloaromatic carboxylic acid groups having from 6 to 14 carbon atoms in the aromatic ring.

5. A branched ester composition comprising at least one ester compound of formula RCOOR' wherein R is a straight chain or branched, substituted or unsubstituted, alkyl or alkenyl group having from about 1 to about 30 carbon atoms or a substituted or unsubstituted cycloaromatic group having from about 6 to about 14 carbon atoms and wherein R' is an alkyl or alkenyl group having from about 8 to about 36 carbon atoms wherein said R' group has an average number of branches per molecule of from about 1.0 to about 3.0, said branching on the R' group comprising methyl and ethyl branches.

6. A personal care composition comprising:
(i) the branched ester composition of claim 1 and;
(ii) a cosmetically acceptable vehicle.

7. A personal care composition comprising:
(i) the branched ester composition of claim 5 and;
(ii) a cosmetically acceptable vehicle.

8. A branched primary alcohol carboxylic acid ester composition wherein the branched alcohol group of the composition has from about 8 to about 36 carbon atoms and an average number of branches per molecule of from about 0.7 to about 3.0, said branching comprising methyl and ethyl branches, and wherein the branched primary alcohol group of the composition comprises less than about 0.5 atom % of quaternary carbon atoms, wherein at least 40 percent of the number of branches in the branched alcohol group are methyl branches and wherein from 5 to 30 percent of the number of branches in the branched alcohol group are ethyl branches.

9. A branched primary alcohol carboxylic acid ester composition wherein the branched alcohol group of the composition has from about 8 to about 36 carbon atoms and an average number of branches per molecule of from about 0.7 to about 3.0, said branching comprising methyl and ethyl branches, and wherein less than 5 percent of the alcohol molecule in the primary alcohol are linear alcohol molecules, wherein at least 40 percent of the number of branches in the branched alcohol group are methyl branches and wherein from 5 to 30 percent of the number of branches in the branched alcohol group are ethyl branches.

10. A branched primary alcohol carboxylic acid ester composition wherein the branched alcohol group of the composition has from about 8 to about 36 carbon atoms and an average number of branches per molecule of from about 0.7 to about 3.0, said branching comprising methyl and ethyl branches, and wherein at least 40 percent of the number of branches in the alcohol group are methyl branches, and wherein from 5 to 25 percent of the branching is on the C2 carbon position relative to the hydroxyl carbon atom.

11. A branched primary alcohol carboxylic acid ester composition wherein the branched alcohol group of the composition has from about 8 to about 36 carbon atoms and an average number of branches per molecule of from about 0.7 to about 3.0, said branching comprising methyl and ethyl branches, and wherein from 5 percent to 30 percent of the number of branches in the alcohol group are ethyl branches.

12. A personal care composition comprising:
(i) the branched ester composition of claim 8 and;
(ii) a cosmetically acceptable vehicle.

13. A personal care composition comprising:
(i) the branched ester composition of claim 9 and;
(ii) a cosmetically acceptable vehicle.

14. A personal care composition comprising:
(i) the branched ester composition of claim 10 and;
(ii) a cosmetically acceptable vehicle.

15. A personal care composition comprising:
(i) the branched ester composition of claim 11 and;
(ii) a cosmetically acceptable vehicle.

* * * * *